United States Patent [19]

Kloetzer et al.

[11] Patent Number: 4,547,318

[45] Date of Patent: Oct. 15, 1985

[54] PREPARATION OF COLOR-STABLE, LIGHT-COLORED, AQUEOUS SALT PASTES OF WASH-ACTIVE, α-SULFOFATTY ACID ESTERS

[75] Inventors: Dietrich Kloetzer, Duesseldorf; Karl-Heinz Linde, Langenfeld; Klaus Ojust, Duesseldorf, all of Fed. Rep. of Germany

[73] Assignee: Henkel KgaA, Duesseldorf, Fed. Rep. of Germany

[21] Appl. No.: 604,100

[22] Filed: Apr. 26, 1984

[30] Foreign Application Priority Data

May 30, 1983 [DE] Fed. Rep. of Germany ........ 3319591

[51] Int. Cl.$^4$ ............................................. C07C 143/90
[52] U.S. Cl. ..................................................... 260/400
[58] Field of Search ......................................... 260/400

[56] References Cited

U.S. PATENT DOCUMENTS

| | | | |
|---|---|---|---|
| 2,195,187 | 3/1940 | Moyer | 260/400 |
| 2,804,466 | 8/1957 | Schurman | 260/400 |
| 3,158,632 | 11/1964 | Koch et al. | 260/400 |
| 3,159,657 | 12/1964 | Weiss et al. | 260/400 |
| 3,256,303 | 6/1966 | Stein et al. | 260/400 |
| 3,354,187 | 11/1967 | Stein et al. | 260/400 |
| 3,452,064 | 6/1969 | Stein et al. | 260/400 |
| 3,485,856 | 12/1969 | Weiss et al. | 260/400 |
| 4,080,372 | 3/1978 | Stein et al. | 260/400 |

FOREIGN PATENT DOCUMENTS 2089793  6/1982  United Kingdom .

*Primary Examiner*—J. E. Evans
*Attorney, Agent, or Firm*—Ernest G. Szoke; Nelson Littell, Jr.; Henry E. Millson, Jr.

[57] ABSTRACT

This invention is directed to a process for the preparation of color-stable, light-colored aqueous salt pastes of wash-active esters of α-sulfofatty acids with monohydric $C_1$–$C_8$-alcohols by a combined bleaching treatment of dark-colored α-sulfofatty acid ester salt paste with hydrogen peroxide and alkali metal hypochlorite. According to the process, dark-colored α-sulfofatty acid ester salt paste is first subjected in a preliminary bleaching step to bleaching with alkali metal hypochlorite in a neutral to mildly alkaline aqueous medium, any excess metal hypochlorite is removed, and the paste is subjected in a final bleaching step to bleaching in a mildly acidic medium with hydrogen peroxide or with one or more compounds which yield hydrogen peroxide.

16 Claims, No Drawings

PREPARATION OF COLOR-STABLE, LIGHT-COLORED, AQUEOUS SALT PASTES OF WASH-ACTIVE, α-SULFOFATTY ACID ESTERS

FIELD OF THE INVENTION

This invention is directed to the preparation of α-sulfofatty acid ester pastes. More specifically, this invention is directed to the preparation of color-stable, light-colored, aqueous salt pastes of wash-active, α-sulfofatty acid esters and wash-active alkyl benzene sulfonates.

BACKGROUND OF THE INVENTION

This invention is based upon the general problem of simplifying the known preparation of wash-active α-sulfofatty acid esters from fats and oils, particularly those of natural origin, in such a way that the fatty acids or fatty acid mixtures of vegetable and/or animal origin can be used as a feasible alternative in the production of modern detergent compositions, thus making it reproducible for large scale technical purposes. In the field of washing and cleaning agents, particularly fabric detergents, the emphasis today is, as is known, on petroleum-based synthetic products although it has been known for decades that high-grade wash-active components can also be obtained from, in particular, the fatty acid triglycerides of natural starting materials.

U.S. Pat. No. 2,195,187, incorporated herein by reference, describes wash-active substances (WAS) based upon α-sulfofatty acids and their esters. They are obtained by sulfonation of lower alkyl esters of saturated higher fatty acids with sulfur trioxide. The lower fatty acid alkyl esters used as starting materials are obtained by transesterification of hydrogenated fats or oils with monofunctional lower alkanols, particularly methanol, or by hydrolysis of the fats or oils, followed by esterification with alkanols.

Later studies with this class of wash-active α-sulfofatty acids and corresponding fatty acid esters, as well as their salts, have been undertaken. U.S. Pat. No. 3,256,303 incorporated herein by reference, for example, describes a process for the production of this class of compounds. Fatty acids and fatty acid esters, which contain from 6 to 28 carbon atoms in the fatty acid radical, which have no other sulfonatable or sulfatizable groups, apart from the α-position carbon atom of the fatty acid radical, and which have an iodine number less than 5, are sulfonated with a sulfur trioxide/inert gas mixture, and the reaction product is neutralized. A parallel process for the production of the same compounds, working with alternate process conditions but at the end with the same means, is described in U.S. Pat. No. 3,158,632, incorporated herein by reference.

One of the main difficulties in this field is the poor color-stability of the fatty acid-containing or fatty acid ester-containing starting material in the sulfonation stage. Dark-colored to black-brown crude products are obtained, which products must be worked up into light-colored products for use in washing and cleaning agents. The color of the crude sulfonation products depends to a certain extent on the working conditions. However, the technical utilization of this interesting possibility of the raw material is prevented by the following fact: the higher the yield (degree of sulfonation) is in the sulfonation step, the darker is the reaction product and the greater are the difficulties of obtaining light-colored end products.

Bleaching of the crude sulfonic acid derivatives has always been required as a final process step. Two particular methods are generally known to the art: acid bleaching with hydrogen peroxide (see, for example, U.S. Pat. No. 3,159,657, incorporated herein by reference), and combination bleaching, where an acid hydrogen peroxide bleaching stage is followed by neutralization of the sulfonated and partially bleached material, followed again by bleaching with hydrogen peroxide or, better still, with hypochlorite (see, for example, U.S. Pat. No. 3,452,064, incorporated herein by reference).

Special difficulties, or problems, regarding discoloration occur when the sulfonation is to be increased to yields of over 90% or even to sulfonation degrees of over 95%, which problems are dealt with extensively in U.S. Pat. No. 3,485,856, incorporated herein by reference. According to this patent, sulfur trioxide has a highly disintegrating effect on saturated fatty acid esters which are free of alcoholic hydroxyl groups, which leads unavoidably to very darkly discolored sulfonation products in the production of highly sulfonated products with a degree of sulfonation of at least 90%, preferably at least 94%, and particularly at least 96%.

The increase in the degree of sulfonation in these ranges is not only of interest for economic reasons, however, since other factors require such high degrees of sulfonation too. Ester sulfonates with a corresponding low degree of sulfonation lead to difficulties in the conventional production of detergent compositions by spray drying. High pluming values appear in the processing of these ester sulfonates. Furthermore, the degree of sulfonation of ester sulfonates is directly related to undesired by-products formed in this reaction, namely, α-sulfofatty acids. These compounds, which are present after neutralization as the disodium salt, are poorly water-soluble and are therefore unsuitable as raw material for detergents. Increasing the degree of sulfonation from 90% to 96% in these ester sulfonates causes, for example, a decrease of this undesired by-product from 25% to 16%.

U.S. Pat. No. 3,485,856, which deals with the last-mentioned problem, suggests that to limit the discoloration and to maintain certain temperatures in the sulfonation reaction, water should be introduced into the sulfonation product in such quantities that sulfuric acid is formed from the existing excess sulfur trioxide and the water, the concentration of the $H_2SO_4$ being in the range of from about 20 to 100% by weight at the start of the following bleaching phase. For the large-scale technical process, however, new difficulties arise, which represent a considerable risk source. The viscosity of the crude sulfonation product is greatly influenced in the strongly acidic range by even the slightest traces of water. Even the addition of 2% by weight of hydrogen peroxide in the form of a 35% by weight solution—with the quantities of water inevitably introduced therewith—to the crude sulfonation product with a $C_{16}$–$C_{18}$-chain length, leads to a sharp viscosity rise. In a continuous industrial scale process, there will be substantial risk that the pipelines will become blocked. The viscosity rise is particularly critical with an addition of from 1.8 to 2.5% by weight of hydrogen peroxide, based upon the weight of the crude sulfonic acid.

The best bleaching method for crude ester sulfonates so far is based upon use of hydrogen peroxide in the strongly acidic range (pH=0), the bleaching effect being particularly pronounced. However, such a procedure involves the risk of the above-described sudden viscosity increase. With highly sulfonated ester sulfonates, even 2% by weight of hydrogen peroxide is not enough to bring the Klett dye number to required low values. After neutralization of the crude sulfonic acid, it is therefore necessary to bleach again with sodium hypochlorite. A reduction in the amount of the bleaching agent with a simultaneous increase of the bleaching time leads to more unfavorable colors and gives rise to a number of other difficulties; Due to the great viscosity increase produced by the addition of, for example, 2% by weight of hydrogen peroxide to the crude sulfonic acid, it is not possible to obtain paste concentrations higher than 28% by weight of WAS in the neutralization step. In this bleaching method there are also problems with foaming, which is difficult to control on an industrial scale. In particular, the foam introduced into the crude sulfonic acid leads to a further increase in viscosity.

The many difficulties appearing in the various stages of the total process lead according to our present knowledge to a forced compromise between sulfonation and bleaching. The optimum degree of sulfonation obtainable in practice is about 90%.

Co-pending, commonly assigned U.S. patent application Ser. No. 288,769, filed July 31, 1981, incorporated herein by reference, describes a possible method of reducing the discoloration of the end sulfonation product by subjecting the fatty acid ester starting material to be sulfonated to an additional purification step. In this modified process, a fatty acid ester fraction, from which the accompanying fatty acid glycerides have been removed to a residual content of at most about 1% by weight, preferably no more than about 0.3% by weight, based upon the material to be sulfonated, is introduced into the sulfonation step. The elimination of these "accompanying fatty acid glycerides" from the esters of the fatty acids or fatty acid mixtures of natural origin with monohydric alcohols requires at least two distillations of the fatty acid ester fraction to be sulfonated.

OBJECTS OF THE INVENTION

It is an object of the invention to provide a simple and reproducible bleaching process for $\alpha$-sulfofatty acid esters or their salts, particularly those based upon fats and oils of vegetable and/or animal origin, which allows high reaction yields to be obtained in the sulfonation step, amounting preferably to more than 95% by weight, more preferably to more than 97% by weight, but which leads to light-colored, color-stable products without any need for redistillation of the fatty acid ester fraction obtained as intermediate product.

It is also an object of the invention to provide highly concentrated aqueous salt pastes of which the WAS-content may amount, for example, to as much as 60% by weight.

It is a further object of the invention to provide a method of bleaching which, when applied on an industrial scale, does not involve any of the above-described safety risks attendant to hydrogen peroxide bleaching of the acid $\alpha$-sulfofatty acid esters, but which nevertheless uses hydrogen peroxide as a substantial component of the bleaching process.

These and other objects of the invention will become more apparent in the discussion below.

DETAILED DESCRIPTION OF THE INVENTION

According to the invention, the above objects are achieved by a combined bleaching treatment which uses the well known bleaching agents hydrogen peroxide and hypochlorite but changes the order in which they are used as compared with hitherto known proposals. In addition, the material to be bleached is formed by the aqueous salt suspensions of the WAS in all stages of the bleaching treatment.

Thus, the present invention relates to a process for the production of color-stable, light-colored, aqueous salt pastes of wash-active esters of $\alpha$-sulfofatty acids with monohydric $C_1$-$C_8$-alcohols ($\alpha$-sulfofatty acid esters), particularly based upon fats and oils of vegetable and/or animal origin, and mixtures thereof with wash-active alkyl benzene sulfonates by subjecting the dark-colored, crude starting material to a combined bleaching treatment with hydrogen peroxide and alkali metal hypochlorite. The process is characterized in that the dark-colored starting material is first subjected to a preliminary bleaching treatment with hypochlorite in a neutral to mildly alkalized aqueous medium, optionally followed by the removal of any hypochlorite still present, after which the salt paste is subjected to final bleaching in the mildly acidic range with hydrogen peroxide or with compounds yielding hydrogen peroxide.

Accordingly, the process according to the invention is also based on a combined bleaching treatment in which the desired bleaching effect is obtained partly by hypochlorite and partly by hydrogen peroxide. However, the crucial difference lies in particular in the combination of the following measures:

The particular order in which the bleaches are used is selected in such a way that most of the bleaching work to be done falls first to the hypochlorite, hydrogen peroxide only being used in a concluding bleaching step, in addition to which both bleaches, i.e., the hydrogen peroxide in particular, are used on the $\alpha$-sulfofatty acid esters present in the salt form. The pH-value of an aqueous suspension of the monosodium salt of $\alpha$-sulfofatty acid esters is known to be of the order of 3.5, so that it follows from this that both bleaching treatments take place in the pH-range above that limit. The first bleaching step with hypochlorite is preferably carried out at a pH value in the range from about 7 to 11, preferably in the range from about 7.5 to 10. The following bleaching treatment with hydrogen peroxide is preferably carried out at a pH value below 7 and, more particularly, at a pH-value in the range from about 4.0 to 6.5. The following particular observations apply to the process according to the invention and to its component stages:

For the preliminary bleaching treatment with hypochlorite, the crude sulfonation product is first converted into the ester sulfonate paste by salt formation on the $\alpha$-sulfofatty acid group. Alkali metal hydroxides and/or amines are normally used for this purpose. The preferred salt-forming neutralizing agent is sodium hydroxide. Hypochlorite is added in the form of an NaOCl solution, approximately 5 to 20% by weight NaOCl solutions and, preferably, approximately 10 to 15% by weight NaOCl solutions being particularly suitable. The NaOCl is normally used in a quantity of up to about 4% by weight, based upon WAS and expressed as 100% substance. Quantities of from about 0.1 to 3% by weight of NaOCl are normally used, again based upon WAS and expressed as 100% substance. This preliminary hypochlorite bleaching treatment is carried out at temperatures in the range from about 50° to 75° C., preferably in the range from about 55° to 70° C. The bleaching time is normally from about 1 to 10 hours, more particularly, from about 1 to 3 hours. The actual bleaching treatment is carried out as follows:

An NaOCl solution having a concentration of, for example, from about 12 to 13% is added to the pH-corrected aqueous ester sulfonate paste. The addition may be made in one or more stages. Thereafter, the color lightening effect which sets in during the bleaching reaction and the chlorine content prevailing in the reaction mixture at the same time are continuously monitored. As the bleaching reaction progresses, a deceleration in the color lightening effect can be observed by measurement, for example, with the aid of photometrically determined color numbers. During the reaction, there is a deceleration in the color lightening effect commensurate with a reduction in the consumption of bleach. As far as the paste color values to be adjusted are concerned, the general rule is that the preliminary bleaching treatment with hypochlorite always passes an optimum bleaching level which is characterized by the lightest color of the paste. After the bleaching effect has passed this optimum level, a more or less drastic color reversal or deterioration in color occurs. In the preferred embodiment of the invention, the preliminary hypochlorite bleaching treatment is terminated at about the same time that this optimum bleaching effect is reached.

This preliminary bleaching step is followed by an intermediate treatment in which any hypochlorite still remaining in the reaction mixture is eliminated. This may be done simply by reducing the pH-value into the mildly acidic range, although it is also possible to add a reducing agent to accelerate removal of the hypochlorite residue, dependent upon its size. Reducing agents particularly suitable for this purpose are aldehydes, particularly formaldehyde, added in small quantities. However, reducing salts, for example, alkali metal sulfites or alkali metal thiosulfates, may also be used for this purpose. The conditions under which this intermediate treatment with reducing agents is carried out may be the same as those under which the preliminary hypochlorite bleaching treatment is carried out. Accordingly, the intermediate treatment in question may be carried out at a temperature in the range from about 50° to 75° C., preferably in the range from about 55° to 70° C., and at pH-values in the same range as those used for the preliminary hypochlorite bleaching treatment. The intermediate treatment generally takes from about 0.5 to 5 hours, more particularly from about 1 to 2 hours.

If necessary, the aqueous ester sulfonate paste is adjusted to lower pH-values in the above-mentioned range, for example, to a pH-value in the range from about 4.5 to 6.5, upon completion of this reaction step. Inorganic or organic acids may be used for this purpose. One preferred acid for pH-regulation is sulfuric acid. The object of this pH reduction is to prepare for the following bleaching treatment with hydrogen peroxide.

The hydrogen peroxide may be used, for example, in quantities of up to about 2.5% by weight, preferably in quantities of from about 1 to 2% by weight, expressed in each case as 100% $H_2O_2$ and based upon WAS. Approximately 20 to 70% by weight of aqueous $H_2O_2$ solutions, for example, are suitable for the hydrogen peroxide bleaching treatment. This final bleaching treatment with hydrogen peroxide is also preferably carried out at temperatures above about 50° C., more particularly in the range from about 55° to 70° C. This final bleaching treatment with $H_2O_2$ produces a further lightening in the color of the ester sulfonate paste. In general, however, the color lightening effect produced by this final bleaching treatment is only limited in comparison with that produced by the preliminary hypochlorite bleaching treatment. However, it is emphasized that the ester sulfonate pastes obtained in accordance with the invention are considerably more color-stable than corresponding pastes bleached solely with sodium hypochlorite. Dependent upon the quantity of $H_2O_2$ used, the hydrogen peroxide bleaching treatment may also last up a few hours, taking for example, up to about 20 hours to complete.

A major advantage of the final bleaching treatment with hydrogen peroxide according to the invention of aqueous paste-form suspensions of the salts of the WAS, as opposed to the as yet unneutralized acidic sulfonation products according to the prior art, lies in the possibility of having and being able to treat comparatively high WAS-concentrations in the aqueous phase without at the same time having any significant safety risks. Thus, it is possible, for example, to work with WAS-contents in the aqueous paste of from about 20 to 30% by weight without any need to add flow promoters and without any danger of blockages in the system as a whole attributable to sudden increases in viscosity. In cases where flow promoters or viscosity regulators are used, the concentration of the WAS in the pastes to be bleached may be increased, for example, to as high as 60% by weight.

Suitable flow promoters and viscosity regulators include, inter alia, relatively high molecular weight compounds containing polyglycol ether groups, such as polyethylene glycols having a molecular weight of from about 600 to 6000, polypropylene glycols having a molecular weight of from about 250 to 4000, adducts of from about 20 to 80 mols of ethylene oxide with aliphatic alcohols containing from about 10 to 20 carbon atoms, and adducts of from about 20 to 60 mols of ethylene oxide with alkyl phenols containing from 6 to 12 carbon atoms in the alkyl group. These compounds are added to the aqueous pastes in quantities of at most 10% by weight, preferably in quantities of from 0.1 to 5% by weight and, more particularly, in quantities of from 0.5 to 3% by weight, based upon the WAS-concentrates.

Other suitable flow promoters and viscosity regulators are $C_1$-$C_6$-alkyl monocarboxylic acids substituted in the α-position by halogen atoms or cyano or sulfo groups, salts or esters thereof with $C_1$-$C_6$-alkanols, particularly with ethanol or methanol, alkylene dicarboxylic acids substituted in the α-position by halogen atoms or cyano or sulfo groups, salts or esters thereof with $C_1$-$C_6$-alkanols, particularly with ethanol or methanol, nitrilotriacetic acid and its salts, and ether alcohols containing from 2 to 4 alkylene glycol ether units and one methoxy or ethoxy group. These compounds are added to the aqueous pastes in quantities of from 1 to 15% by weight, preferably in quantities of from 7 to 12% by weight, based upon the WAS-content.

Other suitable flow promoters and viscosity regulators are $C_8$-$C_{40}$-alcohols which, in addition, may contain one or more hydroxyl groups as substituents, and adducts of up to 20 mols of ethylene oxide and/or propylene oxide with alcohols such as these. These compounds are added to the aqueous pastes in quantities of from about 1 to 15% by weight, based upon the WAS-content.

Finally, N-chlorinated derivatives of aryl sulfonic acid amide-sodium compounds, for example, sodium N-chloro-p-toluene sulfonic acid amide and sodium N-chlorobenzene sulfonic acid amide, may also be used as flow promoters and viscosity regulators. These compounds are used in quantities of from about 0.5 to 10% by weight, based upon the concentrate.

By use of the process according to the invention, it is possible, without any need for redistillation of the fatty acid alkyl esters obtained from natural starting materials, to obtain color values and color stability levels which are at least comparable with those obtained using the best of the hitherto known processes concerned with lightening the color of neutral sulfonation products. This occurs provided measurement is carried out by exactly the same method with the same concentrations of WAS in cuvettes of the same size and with the same layer thickness.

Accordingly, the bleaching process according to the invention fits into a multistage process which produces high-quality surfactant components from natural starting materials, particularly vegetable and/or animal oils. Specifically, certain facts known to those skilled in the art are applicable to carrying out various stages of the entire process according to the invention. These facts are set forth briefly herebelow:

The oils and/or fats used as starting materials can originate from plants or from land or water animals. Their fatty acid radicals primarily contain from about 8 to 18 carbon atoms, fats with from about 10 to 14 carbon atoms in the fatty acid radicals being equally suitable as those with from about 16 to 18 carbon atoms in the fatty acid radicals. Sulfatizable or sulfonatable groups, which should not be present in these fatty acids or their esters—apart from the α-position hydrogen atom of the fatty acid radical—include, for example, double bonds or alcoholic hydroxyl groups. Initial double bonds can be removed, that is saturated, by hydrogenation. It is possible to effect this hydrogenation in the starting fat or oil material, but preferably the fatty acid alkyl ester obtained after glyceride splitting is saturated by hydrogenation. This hydrogenation is effected in known manner. The hydrogenation products should have iodine numbers less than 2, preferably less than 1, and particularly in the range of about 0.5 and less. Preferred starting materials for the subsequent sulfonation step are tallow fatty acid methyl ester and palm oil fatty acid methyl ester.

The material prepared this way is then sulfonated in known manner, for example, at temperatures of from about 70° to 130° C. in a falling film reactor with a mixture of gaseous sulfur trioxide and inert gas during a period of from about 10 seconds to 120 minutes. The degree of sulfonation is preferably more than 90%, particularly more than 92%, and as a rule more than 94%, sulfonation degrees of 95% and over being particularly preferred.

The subsequent bleaching step is carried out in the form according to the invention described in detail in the foregoing. The bleached material may be directly added as such to the slurry for producing the dry detergent. However, it may also be neutralized to form the neutral paste and stored and/or transported in that form. In one embodiment of the invention, the α-sulfofatty acid esters or their preliminary stages are used together with other surfactant components, particularly with alkyl benzene sulfonates (ABS). In this embodiment, it is possible to mix the ABS and the α-sulfofatty acid esters in any ratios, i.e., for example, in ratios of from about 5 to 95% by weight to 95 to 5% by weight.

The following examples are intended to illustrate the invention and should not be construed as limiting the invention thereto.

EXAMPLES

The ester sulfonate pastes used as starting material in Examples 1 to 9 below were produced by the conventional sulfonation of fatty acid methyl esters. The acid component of the methyl esters consisted essentially of saturated $C_{16}$- and $C_{18}$-fatty acids. The sulfonation reaction was carried out at 90° to 95° C. in a three-stage reactor cascade using a mixture of sulfur trioxide and air ($SO_3$-content: 2–8% by volume; $SO_3$-excess: 15–25 mol percent). The crude sulfonation product was neutralized with dilute sodium hydroxide.

All color measurements were carried out photometrically by Klett's method using 5% by weight WAS-solutions in a 4 cm cuvette with a blue filter at 400–465 nm.

EXAMPLE 1

The starting material used was an ester sulfonate paste having a WAS-content of 32% by weight and a Klett color number of 975. The degree of sulfonation amounted to 97%. This material had been obtained by the sulfonation of a tallow fatty acid methyl ester in which 40% by weight of the acid component consisted of $C_{16}$-fatty acid and 60% by weight of $C_{18}$-fatty acid.

In a heatable reaction vessel, 295.6 kg of a 13% by weight sodium hypochlorite solution (38.4 kg of NaOCl) were added with vigorous stirring at 60° to 70° C. to 5000 kg of starting material (1600 kg of WAS). The mixture, which had a pH value of 9.5, was stirred for three hours at 60° to 70° C. Klett color numbers of 320 and 298 were determined after stirring for 1.5 hours and 3 hours, respectively.

The pH-value was then lowered to 4 by the addition of 20% by weight sulfuric acid, after which the mixture was stirred for two hours at 60° to 70° C. before 53.4 kg of a 30% by weight hydrogen peroxide solution (16 kg of $H_2O_2$) were added. The mixture was stirred to 20 hours at 60° to 70° C. Klett color numbers of 265 and 240 were measured after stirring for 3 hours and 20 hours, respectively. The pH-value of the ester sulfonate paste was then adjusted to a pH of 7 by the addition of dilute sodium hydroxide.

EXAMPLE 2

The procedure of Example 1 was repeated, except that the hydrogen peroxide bleaching treatment was carried out with twice the quantity of bleach, i.e., with 106.8 kg of a 30% by weight hydrogen peroxide solution (32 kg of $H_2O_2$). Klett color numbers of 230 and 210 were measured after stirring for 3 hours and 20 hours, respectively.

EXAMPLE 3

In a heatable reaction vessel, 591.2 kg of a 13% by weight sodium hypochlorite solution (76.8 kg of NaOCl) were added with vigorous stirring to 5000 kg of the starting material of Example 1 (1600 kg of WAS) Thereafter the mixture had a pH value of 10.5 and was stirred for four hours at 60° to 70° C. Two hours after the hypochlorite had been added, a Klett color number of 230 was measured. After another two hours, the Klett color number measured 183. A pH value of 4 was then adjusted by the addition of 20% by weight sulfuric acid, after which the mixture was stirred for 2.5 hours at 60° to 70° C. to decompose the unused hypochlorite. Thereafter, 54.3 kg of a 30% by weight hydrogen peroxide solution (16 kg of $H_2O_2$) were added, and the mixture was stirred for another three hours at 60° to 70° C. The ester sulfonate paste, which now had a Klett color number of 155, was adjusted to a pH of 7 by the addition of dilute sodium hydroxide.

EXAMPLE 4

The starting material used was an ester sulfonate paste having a WAS-content of 32% by weight and a Klett color number of 960. The degree of sulfonation amounted to 95%. This material had been obtained by the sulfonation of a tallow fatty acid methyl ester in which 50% by weight of the acid component consisted of $C_{16}$-fatty acid and 50% by weight of $C_{18}$-fatty acid.

As in Example 1, 123.1 kg of a 13% by weight sodium hypochlorite solution (16 kg of NaOCl) were added at approximately 65° C. to 5000 kg of ester sulfonate paste (1600 kg of WAS). The mixture had a pH value of 8 and was stirred for two hours at 60° to 70° C., the Klett color number falling to 450.

The pH value was then lowered to 4 by the addition of 20% by weight sulfuric acid, after which the paste was stirred for another 30 minutes at around 65° C. before 106.8 kg of a 30% by weight hydrogen peroxide solution (32 kg of $H_2O_2$) were added. The mixture was stirred for 20 hours at around 65° C. Klett color numbers of 370 and 330 were measured after 3 hours and 20 hours, respectively. Finally, the pH-value of the ester sulfonate paste was adjusted to 7.5 by the addition of 20% by weight sodium hydroxide solution.

EXAMPLE 5

As in Example 1, 246.2 kg of a 13% by weight sodium hypochlorite solution (32 kg of NaOCl) were added to 5000 kg of the starting material of Example 4 (1600 kg of WAS). The mixture, which now had a pH value of 9.5, was stirred for two hours at about 65° C., the Klett color number falling to 310.

The pH value was lowered to 4 by the addition of 20% by weight sulfuric acid, after which the paste was stirred for one hour at approximately 65° C. before 53.4 kg of a 30% by weight hydrogen peroxide solution (16 kg of $H_2O_2$) were added. The mixture was then stirred for 20 hours at around 65° C. Klett color numbers of 270 and 240 were determined after stirring for 3 hours and 20 hours, respectively. Finally, the pH-value of the ester sulfonate paste was adjusted to a pH of 6.5 by the addition of dilute sodium hydroxide solution.

EXAMPLE 6

The procedure was as in Example 5, except that the hydrogen peroxide bleaching treatment was carried out with twice the quantity of bleach, i.e., with 106.8 kg of a 30% by weight hydrogen peroxide solution (32 kg of $H_2O_2$). Klett color numbers of 230 and 205 were measured after stirring for 3 hours and 20 hours, respectively.

EXAMPLE 7

As in Example 1, 369.3 kg of a 13% by weight sodium hypochlorite solution (48 kg of NaOCl) were added to 5000 kg of the starting material of Example 4 (1600 kg of WAS). Thereafter, the mixture had a pH-value of 10 and was stirred for four hours at about 65° C. After stirring for two hours, the Klett color number of the mixture was 385 and, after stirring for four hours, 325.

After the pH-value had been lowered by the addition of 20% by weight sulfuric acid, the mixture was stirred for 90 minutes at around 65° C. Then, 53.4 kg of a 30% by weight hydrogen peroxide solution (16 kg of $H_2O_2$) were added, after which the mixture was stirred for 20 hours at around 65° C. Klett color numbers of 250 and 220 were measured after stirring for 3 hours and 20 hours, respectively. Finally, the mixture was adjusted to a pH value of 7.0 by the addition of 20% by weight sodium hydroxide solution.

EXAMPLE 8

The procedure of Example 7 was repeated, except that the hydrogen peroxide bleaching treatment was carried out with twice the quantity of bleach, i.e., with 106.8 kg of a 30% by weight hydrogen peroxide solution (32 kg of $H_2O_2$). Three hours after the bleach had been added, the ester sulfonate paste showed a Klett color number of 210. After stirring for 20 hours, the Klett color number had fallen to 170.

EXAMPLE 9

The starting material used was an ester sulfonate paste having a WAS-content of 30% by weight and a Klett color number of 950. The degree of sulfonation amounted to 94%. This material had been obtained by the sulfonation of a tallow fatty acid methyl ester in which 40% by weight of the acid component consisted of $C_{16}$-fatty acid and 60% by weight of $C_{18}$-fatty acid.

In a heatable reaction vessel, 240 kg of a 12.5% by weight sodium hypochlorite solution (30 kg of NaOCl) were added with vigorous stirring at 65° to 70° C. to 5000 kg of starting material (1500 kg of WAS). The mixture, which had a pH value of 9.5, was stirred for two hours at 65° to 70° C., after which a Klett color number of 280 was measured.

Fifty kilograms of a 30% by weight formaldehyde solution (15 kg of formaldehyde) were then added, after which the mixture was stirred for two hours at 65° to 70° C. The pH-value was then adjusted to 6.0 by the addition of 20% by weight sulfuric acid, before 50 kg of a 30% by weight hydrogen peroxide solution (60 kg of $H_2O_2$) were added. After the bleach had been added, the mixture was stirred for ten hours at 65° to 70° C. Thereafter, the paste showed a Klett color number of 252. Finally, the mixture was adjusted to a pH of 6.8 by the addition of 20% by weight sodium hydroxide.

EXAMPLE 10

The starting material used was an ester sulfonate paste having a WAS-content of 30% by weight and a Klett color number of 970. The degree of sulfonation amounted to 96%. This material had been obtained by the sulfonation of a tallow fatty acid methyl ester in which 50% by weight of the acid component consisted of $C_{16}$-fatty acid and 50% of $C_{18}$- fatty acid.

In a heatable reaction vessel, 115.3 kg of a 13% by weight sodium hypochlorite solution (15 kg of NaOCl) were added with vigorous stirring at 60° to 70° C. to 5000 kg of starting material (1500 kg of WAS). The mixture showed a pH value of 7.9. After stirring for 30 minutes, a Klett color number of 960 was measured.

Another 115.3 kg of a 13% by weight sodium hypochlorite solution (15 kg of NaOCl) were then added, after which a pH value of 8.9 was measured in the mixture. The mixture was then stirred for 90 minutes at 60° to 70° C., after which a Klett color number of 450 was measured.

After the addition of another 115.3 kg of 13% by weight sodium hypochlorite solution (15 kg of NaOCl), the mixture showed a pH value of 9.8. It was then stirred for 150 minutes at 60° to 70° C., the Klett color number falling to 255.

Then, 55.7 kg of 13% by weight sodium hypochlorite solution (7.5 kg of NaOCl) were added, increasing the pH value of the mixture to 10.2, followed by stirring for 15.5 hours at 60° to 70° C. Upon completion of the hypochlorite bleaching treatment, i.e., after a total addition of 52.5 kg of NaOCl and after a total stirring time of 20 hours, the Klett color number of the ester sulfonate paste had fallen from the initial value of 970 to 200.

The pH-value of the mixture was then lowered to 4.8 by the addition of dilute sulfuric acid, followed by the addition of 50 kg of a 30% by weight hydrogen peroxide solution (15 kg of $H_2O_2$). The mixture was then stirred for 20 hours at 60° to 70° C., after which it showed a Klett color number of 173. Finally, the pH-value of the ester sulfonate paste was adjusted to pH 7.5 by the addition of 20% by weight sodium hydroxide solution.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of color-stable, light-colored aqueous salt pastes of wash-active esters of α-sulfofatty acids with $C_1$–$C_8$-alkanols consisting essentially of the steps of
(1) subjecting a dark-colored, wash-active α-sulfofatty acid ester with $C_1$–$C_8$-alkanols in the form of an alkali-metal salt paste containing from 20% to 60% by weight of said ester at a pH-value in the range of 7 to 11 and a temperature of from 50° to 75° C. to the action of from 0.1 to 4% by weight of an alkali metal hypochlorite based on wash-active substance (WAS) for a time sufficient to effect substantial bleaching,
(2) removing the hypochlorite excess by lowering the pH-value to the range of from about 4.0 to 6.5 or by the addition of a reducing agent, of both,
(3) subjecting the partially bleached paste to the action of from about 1 to 2.5% by weight of hydrogen peroxide, expressed as 100% $H_2O_2$ and based on WAS, at a pH-value in the range of about 4.0 to 6.5 and a temperature of from 50° to 75° C. for a time sufficient to effect further bleaching, and
(4) recovering a color-stable, light-colored aqueous salt paste of wash-active esters of α-sulfofatty acids with $C_1$–$C_8$-alkanols.

2. The process of claim 1, wherein the α-sulfofatty acid esters are based upon fats and oils of vegetable and/or animal origin.

3. The process of claim 1, wherein the salt pastes comprise mixtures with wash-active alkyl benzene sulfonates.

4. The process of claim 1, wherein the preliminary bleaching treatment is terminated at about the time the optimum bleaching effect is reached.

5. The process of claim 1, wherein the pH-value of said step (1) bleaching treatment is in the range of from about 7.5 to 10.

6. The process of claim 1, wherein the alkali metal hypochlorite used comprises from about 0.1 to 3% by weight of NaOCl, based upon WAS.

7. The process of claim 1, wherein a reducing agent is added and is selected from the group consisting of formaldehyde, alkali metal sulfites, alkali metal thio-sulfates, and mixtures thereof.

8. The process of claim 1, wherein the pH-value of said step (3) bleaching treatment is adjusted by addition of sulfuric acid.

9. The process of claim 1, wherein the hydrogen peroxide is used in quantities of from about 1 to 2% by weight, expressed as 100% $H_2O_2$ and based upon WAS.

10. The process of claim 1, wherein from approximately 10 to 15% by weight NaOCl solutions and from approximately 20 to 70% by weight $H_2O_2$ solutions are used.

11. The process of claim 1, wherein the hypochlorite bleaching treatment is carried out at temperatures in the range of from about 50° to 75° C. over a period of from about 1 to 10 hours.

12. The process of claim 11, wherein the temperatures are in the range of from about 55° to 70° C.

13. The process of claim 11, wherein the treatment is carried out over a period of from about 1 to 3 hours.

14. The process of claim 1, wherein the alkali metal hypochlorite removal step and the final bleaching treatment are carried out at temperatures above 50° C.

15. The process of claim 14, wherein the alkali metal hypochlorite removal step and the final bleaching treatment are carried out at temperatures in the range of from about 55° to 70° C.

16. The process of claim 1, wherein the process is carried out at atmospheric pressure.

* * * * *